United States Patent [19]

Statter

[11] 3,936,271

[45] Feb. 3, 1976

[54] METHOD FOR PROTEIN ANALYSIS
[75] Inventor: Simon Statter, Playa Del Rey, Calif.
[73] Assignee: The Baltimore Spice Company, Baltimore, Md.
[22] Filed: Aug. 28, 1974
[21] Appl. No.: 501,427

[52] U.S. Cl............ 23/230 B; 252/408 R; 426/231
[51] Int. Cl.² ................... G01N 21/20; G01N 33/16
[58] Field of Search ...... 23/230 M, 230 B; 252/408; 426/231

[56] References Cited
UNITED STATES PATENTS
2,057,479  10/1936  Darling .............................. 426/231

OTHER PUBLICATIONS

U. S. Ashworth, Jour. of Food Science, Vol. 36, 509–510 (1971).

Primary Examiner—Morris O. Wolk
Assistant Examiner—Sidney Marantz
Attorney, Agent, or Firm—Burton Scheiner

[57] ABSTRACT

A dye-binding method for the rapid and accurate colorimetric determination of the percentage of protein in meat. The method is accurate irrespective of the degree of denaturization of the protein or coarseness of the meat to be analyzed.

6 Claims, No Drawings

METHOD FOR PROTEIN ANALYSIS

BACKGROUND OF THE INVENTION

This invention relates to a method for the colorimetric determination of the percentage of protein in meat.

The rapid and accurate determination of the percentage of protein in meat is of particular importance to the meat processing industry to assure accurate batch-to-batch composition control whereby product uniformity and cost control may be optimized. For many years the most commonly utilized standard quantitative test for percentage of protein in meat and dairy products was generally considered to be Kjeldahl analysis, and particularly averaged duplicate Kjeldahl analyses.

Because of the length of time involved in carrying out an otherwise heretofore generally acceptable quantitive test such as a Kjeldahl analysis such tests are generally inadequate for in-plant quality and cost control. This is particularly so in large volume rapid meat processing plants utilizing computerized batch component/cost programming. In such plants it is necessary for on-line control purposes to have a rapid and accurate protein determination of all protein containing components of the batch as well as the final batch.

Thus, procedures are desired which combine a sufficient accuracy with simplicity in conducting the procedures. Direct colorimetric procedures are particularly desirable whereby involved analytical procedural steps and flammable or dangerous materials as in Kjeldahl analysis, can be dispensed with.

D. C. Udy, Nature Vol. 178, p 314 1956 and Cereal Chem. Vol. 33, p 190 describes methods for estimating protein in milk and wheat flour by dye binding procedures. In addition the Udy Dye Method adopted as official by the Assoc. Off. Anal. Chem. and U.S. Ashworth, Journal of Food Science, Vol. 36, p 509 (1971) describe methods wherein proteins in meat and egg products are determined colorimetrically by dye binding utilizing Acid Orange 12.

The foregoing conventional colorimetric methods for determination of the percentage of protein in meats exhibit disadvantages as to their accuracy and/or the time required for performance, and accordingly a relatively simple sufficiently accurate control test procedure has not heretofore been attained.

The foregoing dye binding methods depend upon the reaction between Acid Orange 12, a monoazo dye, Colour Index Constitution Number 15970, and the proteins of meat to form insoluble complexes. The complexes can be removed by filtration and the free dye concentration of the filtrate measured colorimetrically. A standard curve relating free dye concentration to mg of protein in the sample as determined by the Kjeldahl method can be prepared for various raw and processed meat products. In the above cited literature it has, for example, been reported that cooking, which effects the degree of denaturization of the protein, has little effect on the dye binding capacity, and therefore little effect upon the accuracy or variation in analysis performed in accordance with the therein described colorimetric methods. In addition, these conventional tests due to the therein described parameters of time and temperature, lead to inaccuracies that are unacceptable for present day computerized batch formulation of processed meat products.

DETAILED DISCUSSION

Generally, the method of the invention comprises the use of a known biological stain and indicator, Acid Orange 12, which is a monoazo dye, Colour Index Constitution Number 15970, which is aqueous solution is a bright orange. The dye reacts with the protein to form insoluble complexes. These complexes are removed by filtration and the free non-bound dye concentration measured colorimetrically. The dye bound to the protein is determined by difference and the dye binding capacity of the meat sample calculated as mg dye bound per mg of protein. Analysis of duplicate meat samples by Kjeldahl are utilized to chart a standard curve relating free dye concentration to mg of protein in the sample. This procedure is carried out for each type of meat product for which rapid accurate colorimetric determination of the protein content is required for on-line production control. The aforementioned Ashworth paper is incorporated by reference herein for the procedure of establishing a standard curve relating free dye concentration to total protein in a sample measured for dye binding.

To insure reaction of the Acid Orange 12 with the protein of the meat sample, the sample is macerated in the presence of an aqueous solution of a weak organic acid so as to emulsify the meat protein on the acid side of the iso-electric point to facilitate binding of the acid dye with the protein. The preferred solution is 0.1 M reagent grade aqueous citric acid solution. The minimum end point temperature at which the emulsification-acidification is accomplished is highly significant, if not critical, to the carrying forth of the method of the present invention.

A known amount of the emulsified, acidified meat sample before any reduction in temperature below the minimum end point temperature is then combined with a given volume of a standardized aqueous buffered solution of Acid Orange 12 dye and the suspension agitated. The dye binding reaction is then permitted to go to completion. The time required for the dye binding reaction to go to completion has been found to vary with the meat sampled, contrary to the prior art teachings which would appear to lead one to assume that a generally fixed reaction time suffices for the protein analysis of any type of meat or meat product. While I do not wish to be bound by this statement, it is theorized that the degree of denaturization of the protein of the meat sample, such as by heat or other denaturants, effects the rate at which the protein forms on insoluble complex with the Acid Orange 12 dye. Therefore reliance upon a fixed reaction time can lead to unacceptable deviation, and thus error in determining the protein content of a meat sample. The now discovered parameters of minimum end point reaction temperature and time are highly significant, if not critical, to the rapid accurate determination of the protein content of meat samples in accordance with the colorimetric method of this invention.

It has been found through considerable experimentation that the critical minimum emulsification-acidification end point temperature is about 40°C and that the time required for the dye binding reaction to go to completion is in the order of about 5 minutes for raw meat or emulsified raw meat and in the order of about 20 minutes for coarse or chopped cooked meat or meat products. In addition, to assure greater sample reliability, the present method preferably emulsifies a sample in preparing the acidified protein emulsion, which is approximately 5 to 40 times that of the procedures of Ashworth and Kjeldahl, for example. In this regard, the present invention is also distinguished procedurally from prior art methods in that a larger amount, approximately double the amount, of emulsified-acidified sample, namely 6 grams is reacted with the buffered aqueous Acid Orange 12 dye solution which is also doubled, namely 50 ml. The increase in the sample size and dye solution does not effect the stoichiometric relation of the reactants but does provide a more representative sample while reducing error due to weighing variations. However, such procedure of increasing accuracy is well recognized in the analytical art and is not considered, per se, to be responsible for the improved analytical results attendant the method of the present invention.

The reacted sample is then filtered and the free non-bound dye in the filtrate colorimetricaly determined by use of a colorimeter set at 475 mu utilizing a 0.3 mm flow-through cuvette. The percentage of protein, by difference, is then determined from the transmisivity of the filtrate as compared to standard charts such as prepared in accordance with the method described by Ashworth. The colorimeter is of course, as in standard procedure, calibrated by use of a reference dye solution. The phosphate buffer solution, reference dye solution, and buffered working reagent dye solution are prepared as follows:

Reference dye solution— dissolve 0.600 g dry Acid Orange 12 (100% dye content) and 1 ml propionic acid in 100 ml warm $H_2O$. Dilute to 1 L with $H_2O$ at 20°C to produce a solution having 42% transmission at 475 mu and a pH of 2.0.

Reagent dye solution— dissolve 1.300 g dry Acid Orange 12 (100% dye content) in 100 ml warm 0.05 M phosphate buffer. Dilute to 1 L with buffer solution at 20°C to produce a solution having 8% transmission at 475 mu.

0.05 M phosphate buffer— dissolve 3.4 g $KH_2PO_4$, 3.4 ml $H_3PO_4$ (1 (85%) + 1) v/v, 60 ml HOAc, 1 ml propionic acid, and 2 g oxalic acid in 800 ml $H_2O$. Dissolve oxalic acid and $KH_2PO_4$ each separately in $H_2O$ then combine with other components. Dilute to 1 L with $H_2O$ at 20°.

It is believed that one skilled in the art can, using the preceding description, carry forth the present invention. The following preferred specific embodiments are, therefore, to be construed as illustrative.

EXAMPLE 1

Emulsified meat and non-cooked meat blend or raw individual meats were analyzed as follows:
a. Weigh out 40 grams of meat sample and place in blender provided with a rotary shear blade;
b. Add 250 ml of 0.1 M citric acid;
c. Emulsify and acidify sample to am homogeneous condition by blending at high speed for 3 to 5 minutes being certain that the temperature of the homogeneous mixture reaches at least 40°C;
d. Weigh 6 grams of homogenate into a bottle and add 50 ml of buffered reagent dye solution and agitate;
e. Calibrate colorimeter with reference dye solution to 42% transmission at 475 mu;
f. Allow the reactants of (d) to stand for about 5 minutes to reach an end point;
g. Filter the reaction product of (f) and determine % transmission of filtrate to light of 475 mu using a 0.3 mm continuous flow cuvette and determine % protein from standard curve established as set forth above.

EXAMPLE 2

Coarse chopped cooked meats, namely smoked hams and shoulders were analyzed by the procedure of Example 1 with the exception that the period of time for the dye binding reaction of (f) was at least 20 minutes.

The following table illustrates additional examples wherein the method of Example 1, for raw meats, and the method of Example 2 for cooked meats was compared with Kjeldahl analyses of the same samples.

Table I

| Sample | | % Protein by Kjeldahl | % Protein by Present Method |
|---|---|---|---|
| 1. | Franks | 12.72 | 13.08 |
| 2. | Raw Bung Bologna Emulsion | 10.88 | 11.26 |
| 3. | Bundle Franks | 11.51 | 11.77 |
| 4. | Franks | 12.18 | 12.22 |
| 5. | Garlic Bologna | 11.04 | 11.36 |
| 6. | Bung Bologna | 11.90 | 12.05 |
| 7. | German Bologna | 12.38 | 12.31 |
| 8. | 1 lb. Franks | 11.32 | 11.62 |
| 9. | Garlic Bologna | 11.81 | 11.93 |
| 10. | Knockwurst | 11.60 | 11.79 |
| 11. | Ham | 14.51 | 14.73 |
| 12. | Knockwurst | 10.91 | 11.32 |
| 13. | 12/1 lb. Franks | 10.89 | 10.66 |
| 14. | Franks | 11.52 | 11.95 |
| 15. | All Beef Franks | 11.39 | 11.36 |
| 16. | All Beef Franks | 11.68 | 11.72 |
| 17. | All Beef Franks | 12.04 | 12.06 |
| 18. | All Beef Franks | 11.63 | 11.48 |
| 19. | All Beef Franks | 11.64 | 11.48 |
| 20. | BBQ | 11.96 | 11.93 |
| 21. | BBQ | 12.12 | 11.93 |
| 22. | BBQ | 11.48 | 12.15 |
| 23. | BBQ | 11.38 | 11.93 |
| 24. | Special Frank | 11.64 | 11.78 |
| 25. | Special Frank | 11.78 | 11.93 |
| 26. | Special Frank | 11.72 | 11.98 |
| 27. | Special Frank | 11.39 | 11.65 |
| 28. | Special Frank | 11.40 | 11.45 |
| 29. | Special Frank | 11.64 | 11.78 |
| 30. | Soy Frank | 12.20 | 12.10 |
| 31. | Soy Frank | 12.12 | 11.72 |
| 32. | Soy Frank | 11.80 | 11.58 |
| 33. | Soy Frank | 12.20 | 12.06 |
| 34. | Soy Frank | 11.78 | 12.28 |
| 35. | Soy Frank | 11.56 | 11.41 |
| 36. | Soy Frank | 11.88 | 11.87 |
| 37. | Soy Frank | 11.79 | 11.78 |
| 38. | Bologna | 11.70 | 11.63 |
| 39. | Bologna | 11.40 | 12.25 |
| 40. | Raw Lean Blend | 14.7 | 14.67 |
| 41. | Raw Fat Blend | 8.2 | 7.87 |
| 42. | Raw Lean Blend | 13.9 | 14.57 |
| 43. | Raw Fat Blend | 8.0 | 8.45 |
| 44. | Raw Lean Blend | 14.1 | 14.7 |
| 45. | Raw Fat Blend | 8.3 | 9.19 |
| 46. | Raw Lean Blend | 13.5 | 13.94 |
| 47. | Raw Fat Blend | 7.5 | 7.83 |
| 48. | Raw Lean Blend | 13.57 | 13.72 |
| 49. | Raw Fat Blend | 6.75 | 6.68 |
| 50. | Raw Lean Blend | 13.89 | 14.28 |
| 51. | Raw Fat Blend | 9.97 | 8.98 |
| 52. | Raw Lean Blend | 13.71 | 14.14 |
| 53. | Raw Fat Blend | 9.74 | 9.71 |
| 54. | Raw Lean Blend | 13.57 | 13.50 |
| 55. | Raw Fat Blend | 10.83 | 10.27 |
| 56. | Raw Lean Blend | 14.88 | 14.31 |
| 57. | Raw Fat Blend | 9.69 | 9.46 |
| 58. | Raw Lean Blend | 14.19 | 15.02 |
| 59. | Raw Fat Blend | 8.85 | 8.76 |
| 60. | Raw Lean Blend | 12.81 | 12.79 |
| 61. | Raw Fat Blend | 7.74 | 7.75 |
| 62. | Raw Lean Blend | 14.03 | 14.74 |
| 63. | Raw Fat Blend | 9.31 | 8.90 |
| 64. | Raw Lean Blend | 12.76 | 12.94 |
| 65. | Raw Fat Blend | 10.24 | 10.85 |
| 66. | Raw Lean Blend | 14.55 | 14.78 |
| 67. | Raw Fat Blend | 9.37 | 9.48 |
| 68. | Raw Lean Blend | 13.41 | 13.71 |

Table I-continued

| Sample | | % Protein by Kjeldahl | % Protein by Present Method |
|---|---|---|---|
| 69. | Raw Fat Blend | 8.91 | 8.89 |
| 70. | Raw Lean Blend | 13.54 | 13.55 |
| 71. | Raw Fat Blend | 9.14 | 8.63 |
| 72. | Raw Lean Blend | 13.6 | 13.63 |
| 73. | Raw Fat Blend | 7.5 | 7.63 |
| 74. | Raw Lean Blend | 13.1 | 13.63 |
| 75. | Raw Fat Blend | 9.1 | 8.13 |
| 76. | Raw Lean Blend | 13.3 | 13.28 |
| 77. | Raw Fat Blend | 9.2 | 8.64 |
| 78. | Raw Lean Blend | 14.1 | 13.9 |
| 79. | Raw Fat Blend | 10.1 | 10.0 |
| 80. | Wiener | 11.7 | 11.48 |
| 81. | Bologna | 11.7 | 11.77 |
| 82. | Wiener | 11.1 | 10.73 |
| 83. | Bologna | 11.2 | 11.35 |
| 84. | Wiener | 11.2 | 11.01 |
| 85. | Bologna | 11.1 | 11.23 |
| 86. | Wiener | 11.3 | 11.10 |
| 87. | Bologna | 11.4 | 11.66 |
| 88. | Wiener | 10.9 | 9.94 |
| 89. | Bologna | 10.9 | 11.10 |
| 90. | Wiener | 10.8 | 9.42 |
| 91. | Bologna | 11.0 | 10.91 |
| 92. | Wiener | 11.5 | 11.2 |
| 93. | Bologna | 11.1 | 11.0 |
| 94. | Wiener | 11.3 | 11.6 |
| 95. | Bologna | 11.0 | 11.4 |
| 96. | Wiener | 11.9 | 11.4 |
| 97. | Bologna | 11.2 | 11.2 |
| 98. | Wiener | 10.9 | 10.7 |
| 99. | Bologna | 11.1 | 10.6 |
| 100. | Wiener | 11.1 | 11.6 |
| 101. | Bologna | 11.2 | 11.1 |
| 102. | Wiener | 11.3 | 11.0 |
| 103. | Bologna | 11.1 | 11.0 |
| 104. | Wiener | 11.2 | 11.1 |
| 105. | Bologna | 11.1 | 10.8 |
| 106. | Wiener | 11.1 | 11.4 |
| 107. | Bologna | 11.3 | 11.3 |
| 108. | Wiener | 11.1 | 11.5 |
| 109. | Bologna | 11.4 | 11.1 |
| 110. | Wiener | 11.5 | 11.5 |
| 111. | Bologna | 11.0 | 11.3 |
| 112. | Wiener | 10.9 | 10.7 |
| 113. | Bologna | 10.7 | 10.6 |
| 114. | Wiener | 12.4 | 12.0 |
| 115. | Bologna | 11.3 | 11.3 |
| 116. | Wiener | 11.0 | 10.8 |
| 117. | Bologna | 10.8 | 11.0 |
| 118. | Wiener | 11.2 | 11.0 |
| 119. | Bologna | 11.5 | 11.1 |

From the foregoing description, one skilled in the art can easily colorimetrically ascertain the percentage of protein of meat products, and without departing from the spirit and scope thereof, can make various changes and modifications of the non-critical aspects of the invention.

I claim:

1. In an Acid Orange 12 dye binding method for the colorimetric determination of the percentage of protein in meat or meat products by emulsification of a sample of the meat or meat products in an acidulant and subsequent reaction with the dye wherein determination of the non-bound dye in a filtrate obtained from the emulsion is utilized to arrive, by difference and reference to a standard curve prepared by a non-colorimetric quantative method, at the percentage protein, the improvement which comprises:
   a. emulsifying the meat and meat products under conditions wherein the temperature of the emulsified-acidified sample emulsion is at least about 40°C; and
   b. reacting the sample emulsion with a solution of the dye before the temperature drops below about 40°C and allowing from about 5 minutes to about 20 minutes for the dye binding reaction.

2. The method of claim 1 wherein the sample of meat or meat product is in the order of about 40 g and is emulsified in the presence of about 250 ml 0.1 M citric acid solution for a period of about 3 to 5 minutes and the dye binding reaction comprises reacting about 6 g of the emulsified-acidified meat sample with about 50 ml of said Acid Orange 12 dye solution.

3. The method of claim 1 wherein the sample being analyzed is raw or emulsified meat and said reaction of (b) reaches an end point in about 5 minutes.

4. The method of claim 1 wherein the sample being analyzed is coarse, chopped, cooked meat and said reaction of (b) reaches an end point after at least about 20 minutes.

5. The method of claim 1 wherein the Acid Orange 12 dye is a buffered aqueous solution having about 8% transmission at 475 mu.

6. The method of claim 1 wherein the emulsification and temperature set forth in (a) is achieved by means of a rotary shear blender.

* * * * *